United States Patent [19]
Errico et al.

[11] Patent Number: 5,669,911
[45] Date of Patent: *Sep. 23, 1997

[54] POLYAXIAL PEDICLE SCREW

[75] Inventors: Joseph P. Errico, Far Hills; Thomas J. Errico, Summit; James D. Ralph, Oakland, all of N.J.

[73] Assignee: Fastenetix, L.L.C., Summit, N.J.

[*] Notice: The term of this patent shall not extend beyond the expiration date of Pat. No. 5,520,690.

[21] Appl. No.: 663,383

[22] Filed: Jun. 13, 1996

Related U.S. Application Data

[63] Continuation-in-part of Ser. No. 559,196, Nov. 13, 1995, which is a continuation-in-part of Ser. No. 421,087, Apr. 13, 1995, Pat. No. 5,520,690.

[51] Int. Cl.⁶ ................................................. A61B 17/70
[52] U.S. Cl. ................................................. 606/61; 606/73
[58] Field of Search ................................ 606/61, 60, 72, 606/73, 69, 70, 71, 59, 54; 623/17

[56] References Cited

U.S. PATENT DOCUMENTS

5,207,678  5/1993  Harms et al. ............................ 606/61

Primary Examiner—Guy V. Tucker
Attorney, Agent, or Firm—Joseph P. Errico

[57] ABSTRACT

A polyaxial orthopedic device for use with rod implant apparatus includes a screw having a curvate head, a locking collar disposed therearound, and a receiving member having a linearly tapered tapered socket in which the screw and the collar are nested. The locking collar is slotted and tapered, and has a semi-spherical interior volume into which the screw head is initially polyaxially held. The receiving member has a transverse channel formed in it for receiving a rod, and an axial bore having a linearly tapered chamber in the bottom portion thereof. The collar is inserted down the bore from the top to seat in the chamber, and the screw is subsequently inserted up through the bottom of the bore and into the collar. The linear taper of the chamber provides a radially inward force on the locking collar when the collar is forced downward therein. This radially inward force causes the locking collar to crush lock against the head of the screw, therein locking the two at the given angulation. It is the placement of the rod in the transverse channel, against the top of the collar, and the subsequent locking down of the rod in the channel which provides the downward force against the locking collar, which in turn locks the screw in its given angulation.

20 Claims, 9 Drawing Sheets

POLYAXIAL PEDICLE SCREW

CROSS-REFERENCE TO PRIOR APPLICATION

This application is a continuation-in-part of prior application U.S. Ser. No. 08/559,196, entitled "A Polyaxial Locking Screw And Coupling Element", filed Nov. 13, 1995, still pending, which is, in turn, a continuation-in-part of application U.S. Ser. No. 08/421,087, entitled "Anterior Spinal Polyaxial Locking Screw Plate Assembly", filed Apr. 13, 1995 and issued May, 28, 1996, now U.S. Pat. No. 5,520,690.

BACKGROUND OF THE INVENTION

1. Field of the Invention

This invention relates generally to a polyaxial screw and coupling apparatus for use with orthopedic fixation systems. More particularly, the present invention relates to a screw for insertion into spinal bone, and a coupling element polyaxially mounted thereto, via a slotted taper ring, for coupling the screw to an orthopedic implantation structure, such as a rod, therein enhancing the efficacy of the implant assembly by providing freedom of angulation among the rod, screw and coupling element.

2. Description of the Prior Art

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic and lumbar spine. For the purposes of this disclosure, however, the word spine shall refer only to the cervical region.

Figure 1:
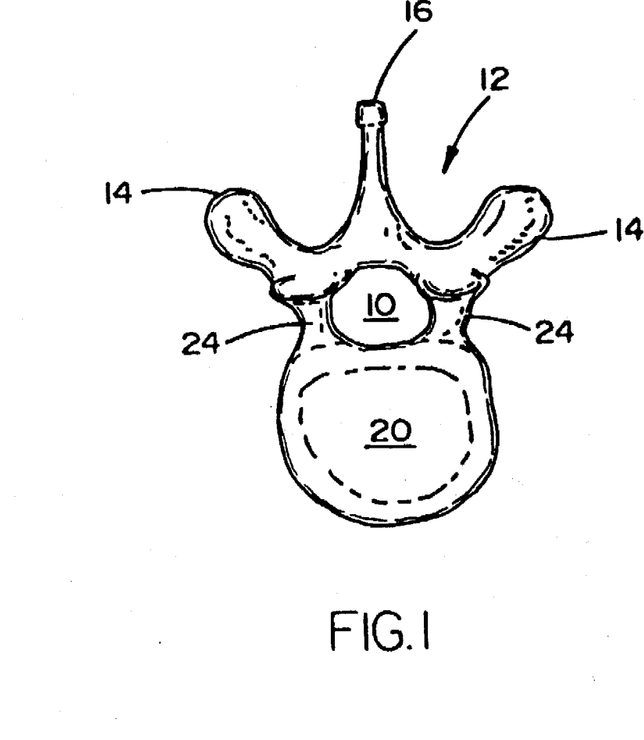
FIG. 1 is a top view of a human vertebra, which is representative of the type for which the present invention is useful for coupling thereto a rod apparatus.
Figure 2:
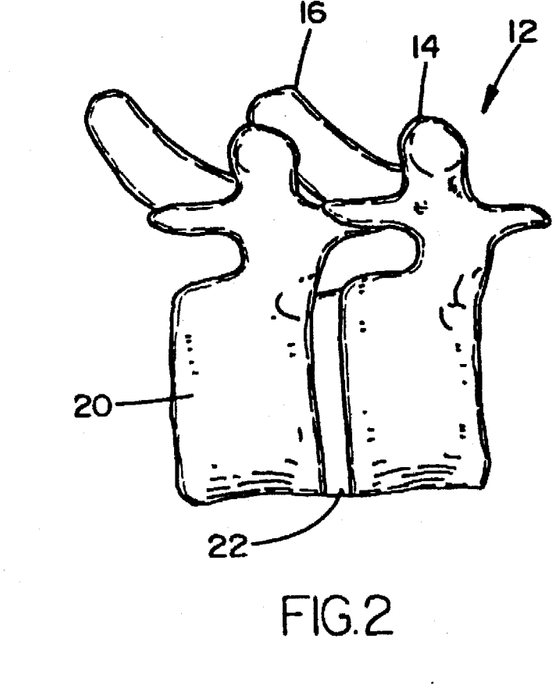
FIG. 2 is a side view of a pair of adjacent vertebrae of the type shown in FIG. 1.
Figure 3:
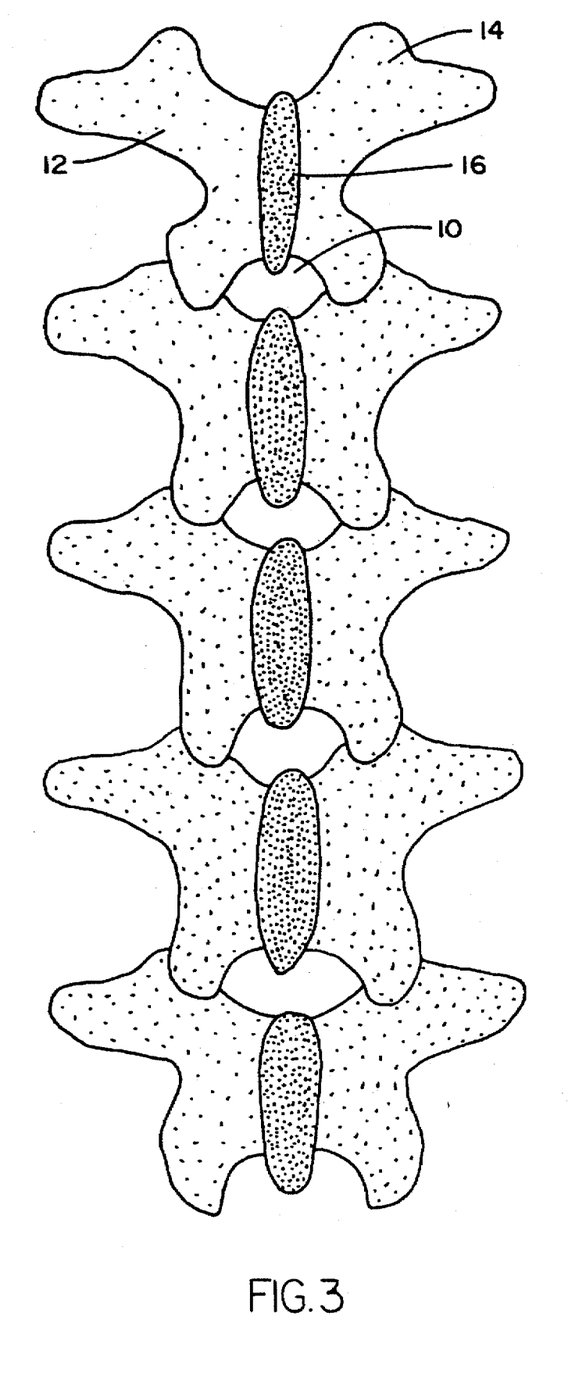
FIG. 3 is a posterior view of a sequence of vertebrae of the type shown in FIGS. 1 and 2.

Referring now to FIGS. 1, 2, and 3, top, side, and posterior views of a vertebral body, a pair of adjacent vertebral bodies, and a sequence of vertebral bodies are shown, respectively. The spinal cord is housed in the central canal 10, protected from the posterior side by a shell of bone called the lamina 12. The lamina 12 includes a rearwardly and downwardly extending portion called the spinous process 16, and laterally extending structures which are referred to as the transverse processes 14. The anterior portion of the spine comprises a set of generally cylindrically shaped bones which are stacked one on top of the other. These portions of the vertebrae are referred to as the vertebral bodies 20, and are each separated from the other by the intervertebral discs 22. The pedicles 24 comprise bone bridges which couple the anterior vertebral body 20 to the corresponding lamina 12.

The spinal column of bones is highly complex in that it includes over twenty bones coupled to one another, housing and protecting critical elements of the nervous system having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classifications suggest, lateral and anterior assemblies are coupled to the anterior portion of the spine, which is the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles.

"Rod assemblies" generally comprise a plurality of such screws which are implanted through the posterior lateral surfaces of the laminae, through the pedicles, and into their respective vertebral bodies. The screws are provided with upper portions which comprise coupling elements, for receiving and securing an elongate rod therethrough. The rod extends along the axis of the spine, coupling to the plurality of screws via their coupling elements. The rigidity of the rod may be utilized to align the spine in conformance with a more desired shape.

It has been identified, however, that a considerable difficulty is associated with inserting screws along a misaligned curvature and simultaneously exactly positioning the coupling elements such that the rod receiving portions thereof are aligned so that the rod can be passed therethrough without distorting the screws. Attempts at achieving proper alignment with fixed screws is understood to require increased operating time, which is known to enhance many complications associated with surgery. Often surgical efforts with such fixed axes devices cannot be achieved, thereby rendering such instrumentation attempts entirely unsuccessful.

The art contains a variety of attempts at providing instrumentation which permit a limited freedom with respect to angulation of the screw and the coupling element. These teachings, however, are generally complex, inadequately reliable, and lack long-term durability. These considerable drawbacks associated with prior art systems also include difficulty properly positioned the rod and coupling elements, and the tedious manipulation of the many small parts in the operative environment.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a polyaxial pedicle screw having a screw having a threaded shaft and a semi-spherical shaped head, a receiving member or coupling element for use with rod stabilization and immobilization systems in the spine. More particularly, the polyaxial screw and receiving member assembly of the present invention comprises a bone screw having a head which is curvate in shape, for example semi-spherical, a slotted and tapered locking collar flexibly mounted to the head of the screw, and a coupling element (or receiving member) in which the collar is securely retained, so that the screw may initially be free to rotate relative to the locking collar and the receiving member, prior to the secure fixation of the rod thereto, but which may be securely locked to the collar (and indirect contact, to the receiving member) at a given angulation once the rod is received.

The coupling element or receiving member has an upper portion and a lower portion, and an axial bore. The upper portion includes a single hole or channel for receiving a rod therein, and the lower portion has an axially tapered interior surface portion for retaining, and providing radial compression force against the slotted and tapered locking collar. The locking collar initially flexibly retains the head of the polyaxial screw, but upon compression downward along the tapered portion of the receiving member, the locking collar compresses inwardly to lock to the head of the screw.

The coupling element or receiving member further comprises either an interior or exterior threading thereon for receiving a top locking nut.

The locking collar comprises a short hollow cylindrical section, having an exterior taper and a semi-spherical interior surface. This interior surface is ideally suited for holding therein the semi-spherical head of the screw. The top of the locking collar is open so that a screwdriving tool, for example an allen wrench or threaded post, may be used in conjunction with a corresponding recess in the semi-spherical head of the screw to drive it into the desired vertebral bone. The locking collar also includes an axial slot, such that the application of the radially inward force by compression into the tapered portion of the axial bore may thus narrow the slot and narrow the interior volume. Conversely, the application of a radially outward force causes the slot to expand and the interior volume to increase. In an unforced state, the head of the screw and the collar remain free to swing relative to one another, however, the application of a radially inward force causes the interior surface of the collar to contract against the head of the screw, thereby crush locking the two elements together.

The coupling element or receiving member comprises a cylindrical body having a cylindrical bore extending axially therethrough. The diameter of the bore is sufficient to permit the the locking collar to slide loosely from the top of the bore to the bottom. An inwardly extending annular lip may be provided to prevent the locking collar from sliding back up the bore once it has passed.

The bottom of the bore tapers linearly inward, to a diameter which is less than the loose (non-radially compressed) locking collar, such that when the locking collar is forced downward as far as it can be pushed, the collar is radially compressed so that the head of the screw can be locked to it.

The axial bore of the receiving member is insufficiently wide, however, for the screw to be passed through it, either with the locking collar mounted around its head, or for the screw to pass if the collar is already positioned. The screw is, therefore, inserted through the bottom of the bore; the head being inserted upwardly into the receiving chamber of the receiving member, and into the locking collar.

The rod receiving upper portion of the coupling element comprises a single transverse channel or hole wherein the rod of the implant apparatus is mounted. More particularly, the walls of the hollow cylindrical body comprise a pair of upwardly extending memebers which define therebetween a single channel across the element. The rod is received in this channel. The bottom surface of the channel, or hole, is curvate for receiving thereon the rod.

In its initial, unlocked position (prior to being forced downward to the bottom of the axial bore of the element), the top of the locking collar rests higher than the curvate bottom of the channel, such that when the rod is placed therein, it seats against it and not the curved bottom of the channel.

The upper portion of the upwardly extending members of the element comprise a surface threading thereon (either the outside or inside surfaces) on which a locking means may be disposed and translated downwardly. If a rod is disposed in the channel, the downward translation of the locking device provides a corresponding downward force onto the rod. The downward force on the rod translates into a downward force on the locking collar causing it to be forced downward into the tapered bottom of the bore (or conversely, the relative motion of the collar and the receiving member may be described as the translation of the locking device on the threading drawing the receiving member upward while holding the locking collar in place). This relative motion of the locking collar into the tapered bottom of the bore causes the rod to seat against the curved bottom of the channel, the screw to be angularly locked in the locking collar, and the locking collar to be locked within the bottom of the receiving member.

In a preferred variation, the locking device may comprise a unitary cap nut having rim and post elements which are joined, but which are free to rotate independently. The threading may be on the exterior of the post or on the interior of the rim, according to the thread location on the receiving member. These alternate variations of the unitary locking device are disclosed more fully in co-pending application U.S. Ser. No. 08/641,504, entitled, "A Unitary Locking Cap For Use With A Pedicle Screw", filed May 1, 1996, assigned to the assignee of the present invention. In either variation, the unitary locking device seats against the rod and prevents it from moving translationally, axially and rotationally.

The first step in the process of implanting this invention is to insert the locking collar into the receiving member, through the top of the bore. Subsequent to the positioning of the collar in the receiving chamber, the head of the screw is inserted through the bottom of the receiving member, into the collar. This may be done prior to the surgery, such as by a surgical assistant, or even at the manufacturing site. The screw and the collar, are then coupled and seated within the linearly tapered chamber of the receiving member. At this point, the screw remains rotationally free to angulate relative to the locking collar, which is in turn inhibited from rotating by its positioning in the tapered chamber of the receiving member.

Once the screw has been so positioned, the screw/locking collar and the receiving member are aligned with respect to one another so that the appropriate screwdriving tool may be inserted down the axial bore, into the recess in the head of the screw, and used to rotate the bone screw into the bone.

Subsequent to the insertion of the screw, the screwdriving tool may be removed from the assembly and the receiving member and the collar which is held by the member, are flexibly and polyaxially rotated to change their angular alignment relative to the screw. Although the locking collar has not yet been driven downwardly into full locking engagement with the bottom of the axial bore, and correspondingly with the head of the screw, the locking collar is sufficiently constrained by the axial bore such that the collar and the coupling element mutually angulate relative to the screw. In fact, it is the angulation freedom of the locking collar relative to the screw which defines the range of angles through which the receiving member may be angulated.

The rod of the implantation apparatus is then provided into the rod receiving channel, and is positioned so that it seats against the top of the locking collar, which is slightly above the curvate bottom of the channel. The locking device is then introduced onto the threaded upwardly extending members until the bottom of the nut or post portions seats against the top of the rod. Continued tightening of the nut causes the receiving member to be drawn upward and/or the locking collar to be driven downward, so that the collar is compressed in the linearly tapered bottom of the axial bore. The mutual engagement of the linear tapers of the bore and the collar thereby providing the compression force against the screw. This causes the screw head to be crush locked within the locking collar and the collar within the coupling element.

Multiple screw and receiving member assemblies are generally necessary to complete the full array of anchoring sites for the rod immobilization system, however, the screw and receiving member assembly of the present invention is designed to be compatible with alternative rod systems so that, where necessary, the present invention may be employed to rectify the failures of other systems the implantation of which may have already begun. For example, it is contemplated that this invention may alternatively be embodied with a side channel, instead of a top channel, wherein the rod is received by the coupling element in its side. Such a variation may further require the use of a rod securing sleeve in conjunction with the locking nut. Such a sleeve may comprise a hollow cylindrical body, having a curvate bottom surface for engaging a rod, and which fits over the top of the element to seat against the rod. The locking nut of a side loading variation engages the sleeve, and the sleeve in turn engages the rod.

BRIEF DESCRIPTION OF THE FIGURES

FIG. 5 is a side view of the coupling element of present invention, wherein critical interior features of the element are shown in phantom.

FIGS. 7a and 7b are a side cross-sectional views of top locking nuts which are aspects of the present invention; wherein FIG. 7a shows a simple open nut, and wherein FIG. 7b shows a cap nut having a central post.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 4:
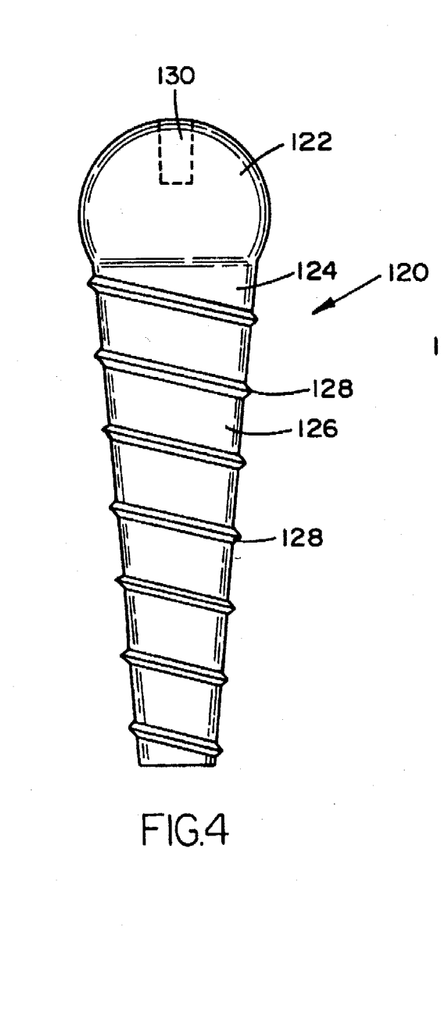
FIG. 4 is a side view of a screw having a curvate head which is an aspect of the present invention.

Referring now to FIG. 4, a side view of the screw portion of the present invention, comprising a curvate head, is shown. The screw 120 comprises a head portion 122, a neck 124, and a shaft 126. In FIG. 4, the shaft 126 is shown as having a tapered shape with a high pitch thread 128. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 122 of the screw 120 comprises a semi-spherical shape, which has a recess 130 in it. It is understood that the semi-spherical shape is a section of a sphere, in the embodiment shown the section is greater in extent than a hemisphere, and it correspondingly exhibits an external contour which is equidistant from a center point of the head. In a preferred embodiment, the major cross-section of the semi-spherical head 122 (as shown in the two dimensional illustration of FIG. 4) includes at least 270 degrees of a circle.

The recess 130 defines a receiving locus for the application of a torque for driving the screw 120 into the bone. The specific shape of the recess 122 may be chosen to cooperate with any suitable screw-driving tool. For example, the recess 130 may comprise a slot for a screwdriver, a hexagonally shaped hole for receiving an allen wrench, or most preferably, a threading for a correspondingly threaded post. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head portion 122 is connected to the shaft 126 at a neck portion 124. While it is preferable that the diameter of the shaft 126 be less than the diameter of the semi-spherical head 122, the neck 124 of the screw 120 may have an equal width to the shaft 126. This preferable dimension permits the screw to swing through a variety of angles while still being sufficiently thick to minimize the risk of screw breakage at the neck (as set forth more fully with respect to FIGS. 5, 8–9, and 11).

Figures 5, 7A, 7B:
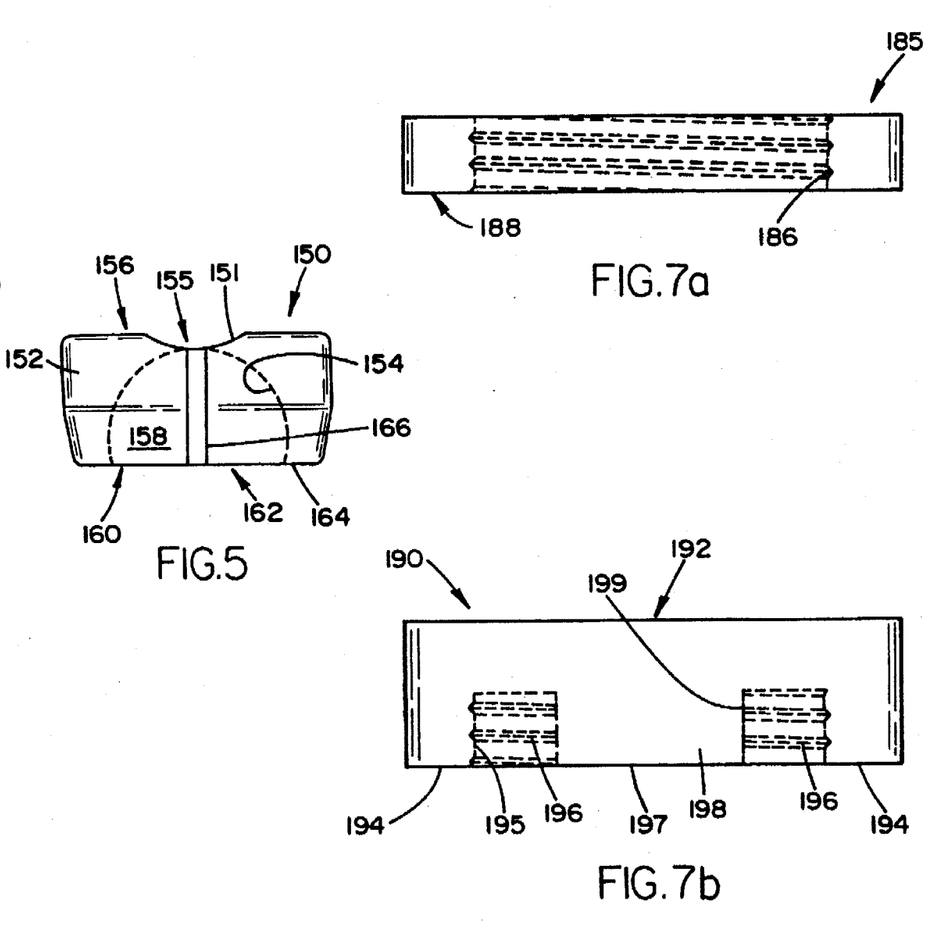

Referring now to FIG. 5, the locking collar of the present invention is shown in a side view, wherein phantom lines show the interior structure of the elements along a diametrical cross section. The locking collar 150 comprises a slotted and tapered cylindrical body 152 having a semi-spherical interior surface 154. The top surface 156 of the locking collar 150 has an opening 155 through which the screw-driving tool which is used to insert the screw 120 into the bone may access and rotate the screw 120 through the collar 150. In addition, the top surface 156 of the collar 150 may also comprise a pair of opposing notches 151 which are curvate and ideally suited for the rod 250 to seat thereon.

The interior semi-spherical volume 158 is ideally suited for holding the head portion 122 of the screw 120, and permitting the screw to rotate through a range of angles. The bottom 160 of the locking collar 150 has a circular hole 162, defined by annular lip 164, which forms the bottom entrance into the interior semi-spherical volume 158. It is understood that the head 122 of the screw 120 is held within the interior semi-spherical volume 158 by the relative size of the head 122 as compared with the openings 155 and 162. More specifically, the annular lip 164 defines the circular opening 162 which has a diameter less than the diameter of the semi-spherical head 122 of the screw 120.

In order that the head 122 of the screw 120 may be inserted into the locking collar 150, the collar is slotted, perferably with a single axial slot 166, extending the entire length of the collar, thus rendering the collar an incomplete circle. This permits the collar 150 to be opened or closed, narrowed or expanded, in accordance with the application of radial forces directed thereto. (It is understood that a series of slots in the lower portion of the collar 150 may similarly permit expansion and narrowing of the interior volume 158, however, the single slot 166 design is preferable it provides for nearly equal expansion and contraction of the entire interior surface 154 of the collar 150 upon the application of a radial force.) The slot 166 permits the head portion 122 to be inserted into the interior volume 158 of the locking collar 150, so that while being rotationally free to move once disposed therein, the head 122 may not be easily removed.

Figure 6:
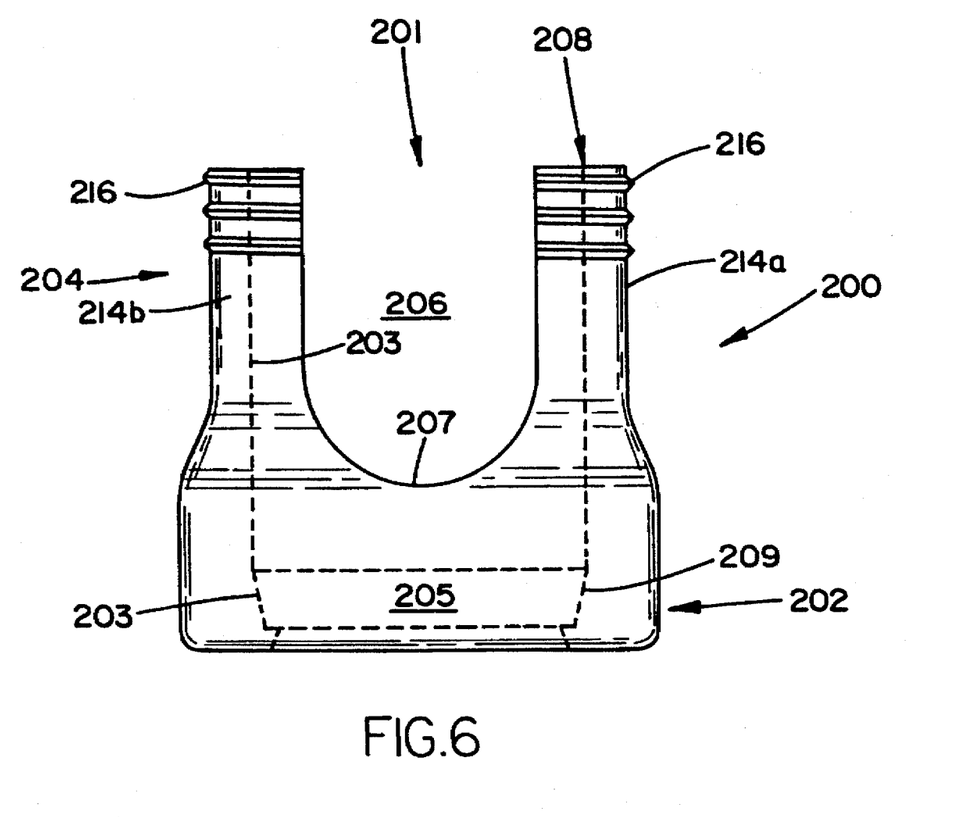
FIG. 6 is a side view of a first coupling element of the present invention wherein interior features of the element are shown in phantom.

Referring now to FIG. 6, the receiving member 200 of the present invention is shown in a side view, wherein critical features of the interior of the element are shown in phantom. The receiving member 200, which comprises a generally cylindrical tubular body having an axial bore 201 extending therethrough, may be conceptually separated into a lower portion 202, and an upper portion 204, each of which shall be described more fully hereinbelow.

First, with respect to the lower portion 202, the interior surface 203 of the axial bore 201 is linearly tapered inwardly at the bottom thereof. Above this linearly tapered chamber 205 may be a small inwardly directed annular lip (not shown). The diameter of the remainder of the axial bore 201 is such that the locking collar 150 may be inserted downwardly therethrough by applying a small radially inward force against the collar 150. The inwardly tapered region at the bottom of the axial bore, however, defines a receiving portion 205, into which the locking collar 150 may be loosely disposed (without inward pressure being applied). The screw 120, and more particularly the head 122 thereof, is inserted through the bottom opening of the receiving member 200 and into the loose locking collar 150. Prior to the locking collar 150 and the head of the screw 122 being fully driven into the socket 205, the screw 120 may be angulated relative to the locking collar 150, and the receiving member (by virtue of the fact that the collar is prohibited from such motion by its disposition in the receiving portion of the receiving member). Once driven fully into the receiving socket 205, however, the linear taper of the interior surface 203 of the axial bore 201 provides the necessary inwardly directed radial force to cause the locking collar 150 to crush lock to the head 122 of the screw 120.

The upper portion 204 of the receiving member 200 includes a vertically oriented slot 206 having a rounded bottom surface 207. This slot 206 forms a rod receiving channel descending downward from the top 208 of the coupling element 200. The channel, in turn, divides the wall cylindrical body of the upper portion 204 into a pair of upwardly extending members 214a,214b. As shown in the embodiment illustrated in FIG. 6, the vertical distance from the top 208 of the channel to the curvate bottom 207 thereof, is larger than the diameter of the rod which is to be provided therein. In addition, the depth of the bottom curvate surface 207 of the channel is such that the top of the locking collar 150 is thereabove, prior to its being completely forceably driven downward into the linearly tapered receiving portion 205.

The top 208 of the upper portion 204, which comprises upwardly extending members 214a,214b, have disposed thereon a threading 216. This threading 216 thereon, is ideally suited for receiving a locking device (see FIGS. 7a and 7b). The nut of FIG. 7a is of a standard variety, and easily mates to a threading on the surface on the outer surface of the upwardly extending elements of the receiving member.

With respect to the variation of the top locking nut of FIG. 7b, the locking nut may further comprise a cap nut having a central post. In such a design, the nut includes a circular top portion 192, having an annular flange portion 194 extending downwardly therefrom at the periphery thereof. The interior surface 196 of this flange portion 194 comprises a threading 195 which is designed to engage the threading 216 of the upwardly extending members 214a,214b. A cylindrical post 198 is positioned at the center of the undersurface of the circular portion 192, such that the distance between the exterior surface 199 of the central post 198 and the inner threaded surface 196 of the flange portion 194 is sufficient for the upwardly extending members 214a, 214b, on which the threadings 216 are disposed, to be engaged by the cap nut. Once fully engaged, the central post 198 provides enhanced strength to the upwardly extending members 214a, 214b, so that they will not bend inwardly, toward one another, thus weakening the locking nut's holding ability. In addition, if the central post is sufficiently long, the bottom 197 thereof may be used to seat against the rod 250 (see FIG. 9) to enhance the locking thereof to the receiving member 200.

It shall be understood that there exist alternative embodiments of the receiving member and the locking device, such as the unitary locking devices set forth in co-pending application U.S. Ser. No. 08/641,504, entitled "A Unitary Locking Cap For Use With A Pedicle Screw".

Figure 8:
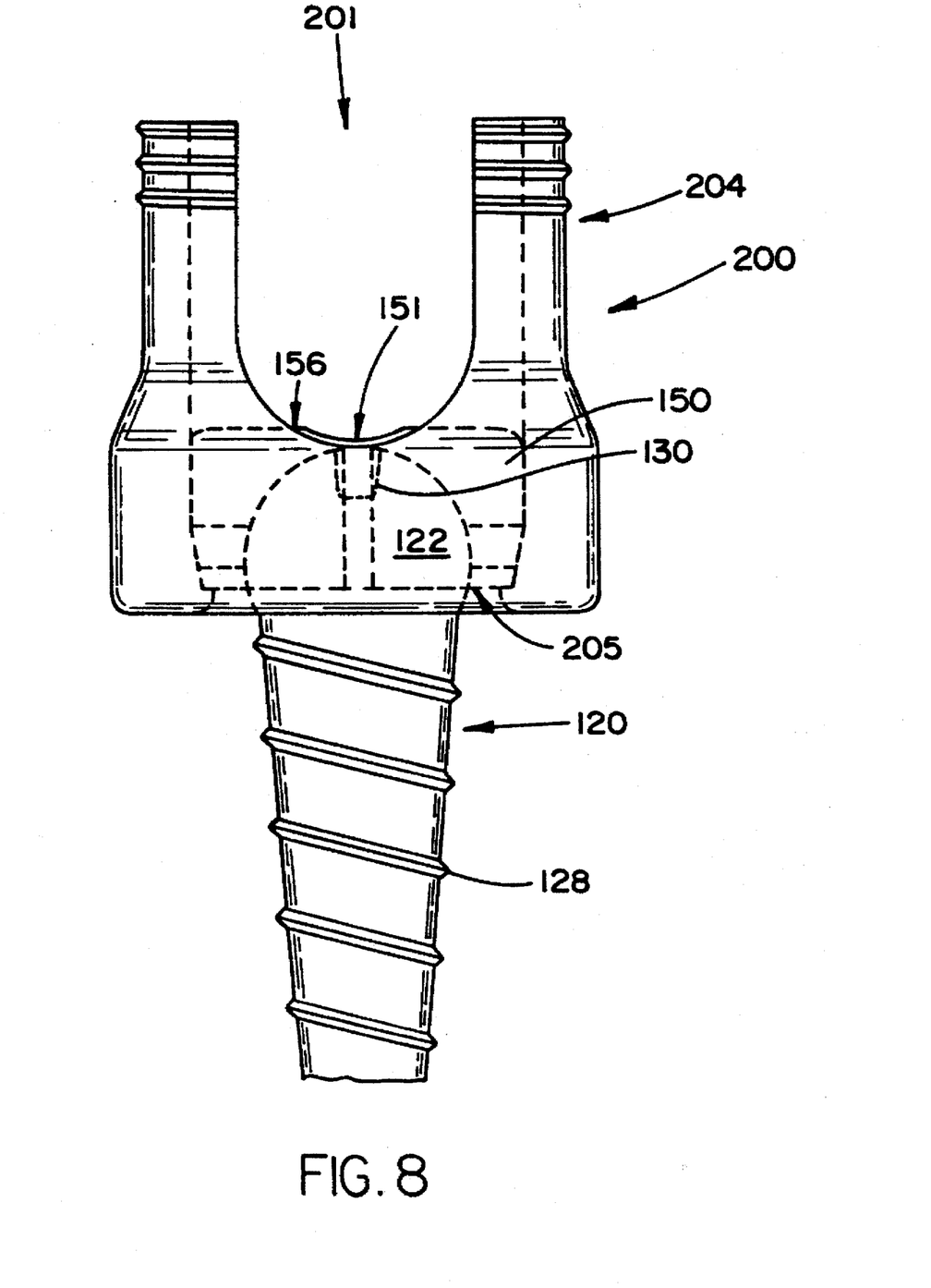
FIG. 8 is a side cross-sectional view of a first embodiment of the present invention in its semi-assembled disposition having the screw and locking collar disposed in the coupling element.
Figure 9:
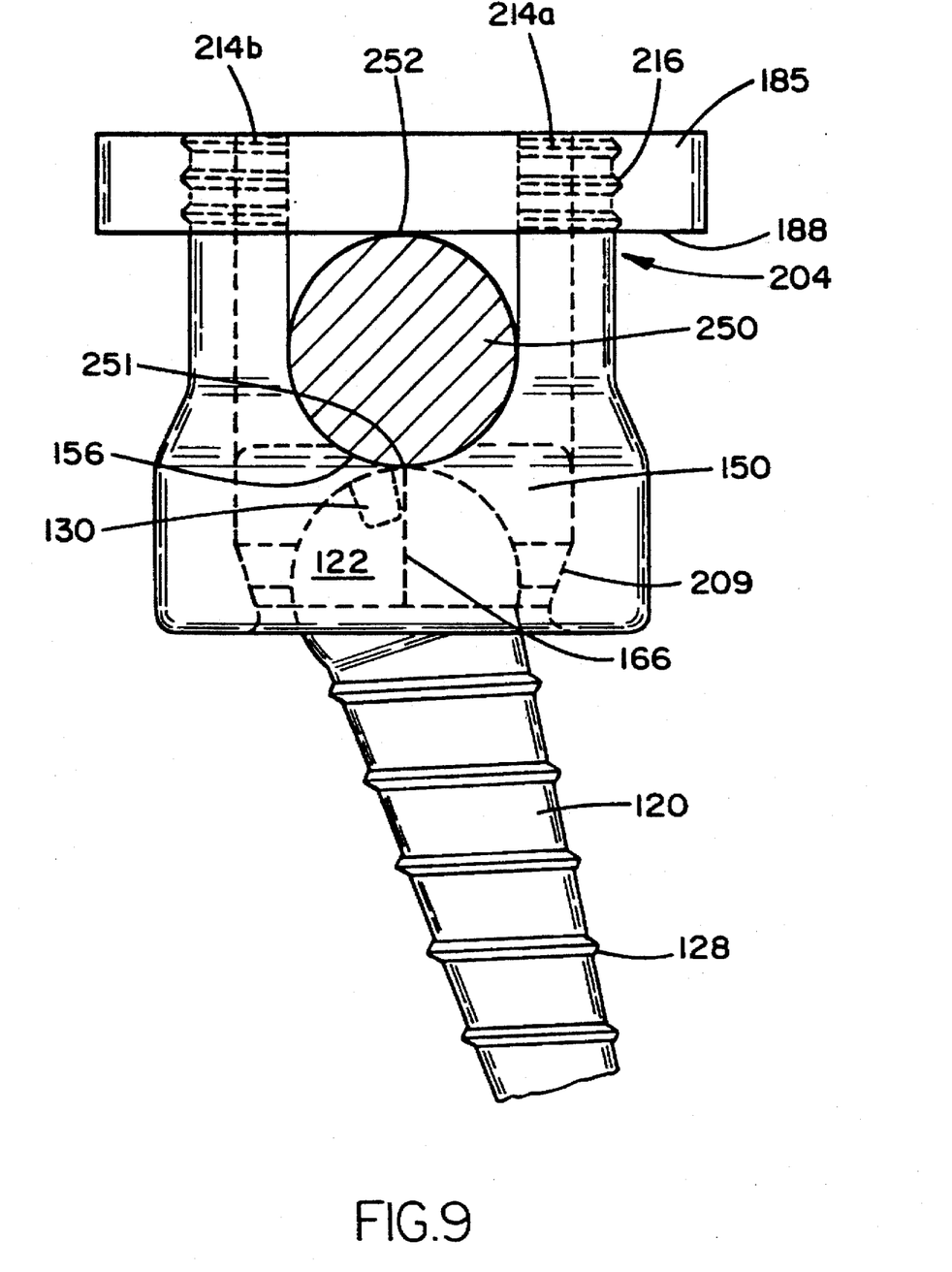
FIG. 9 is a side cross-sectional view of the first embodiment of the present invention in its fully assembled disposition having a rod securely locked therein.

Referring now to FIGS. 8 and 9, which show side views of the initial disposition of the screw, collar, and receiving member and the fully locked receiving member, rod, collar and screw system, respectively, the preferred method of implantation and assembly is described hereinbelow. First, the locking collar 150 is inserted downwardly through the axial bore 201 until it is loosely seated in the linearly tapered receiving chamber 205. The head of the screw 120 is then inserted from the bottom of the receiving chamber 205 into the interior volume 158 of the locking collar 150. Once the device is pre-assembled in this manner, a pre-drilled hole is provided in the bone, into which it is desired that the screw 120 be disposed. The hole may be pre-tapped, or the external threading 128 of the screw 120 may include a self-tapping lead edge. The screw 120 is then aligned relative to the locking collar 150 and the receiving member 200 such that a screwdriver may be inserted through the axial bore 201 and drive the screw 120 into the bone. At this point in the assembly process, the screw 120 and the locking collar 150 have the capacity to rotate relative to one another, while the seating of the locking collar 105 in the receiving portion 205 prevents relative motion of the collar and the receiving member.

In order to ensure that relative rotational motion of the locking collar and the receiving member is prevented, a portion of the axial extent of the locking collar may include an exterior circumferential arc section which is flat, and a corresponding flat surface on the interior surface of the axial bore. The mutual engagement of the flat portions prevents the locking collar from rotating, but not from sliding axially within the axial bore. Axial translation is generally prevented because the head of the screw 120 is inserted in the collar 150, and this prevents the collar from deflecting inwardly and being removed. In the initial position, the top surface 156 of the locking collar 150 is disposed above the curvate bottom of the channel of the upper portion 204 of the receiving member 200, such that the notches 151 of the collar 150 are generally aligned with the channel.

Subsequent to the screw 120 being driven into the hole, the receiving member 200 and the locking collar 150 may be rotated and angulated relative to the screw 120, to an angle such that support rod 250 may be properly nested within the channel. In this initial disposition, however, the bottom 251 of the rod 250 seats on the top surface 156 of the locking collar 150 and not fully on the bottom curved surface of the channel.

Referring now to FIG. 9, after the rod 250 has been appropriately positioned, the locking device 185 is threaded onto the threading 216 of the upwardly extending members 214a, 214b. The lower surface 188 of the locking device 185 seats against the top surface 252 of the rod 250. As the locking device 185 rotates, and descends, relative to the coupling element 200, the rod 250 is driven downward, causing the rod 250 and the locking collar 150 to translate downward slightly. This downward translation causes the tapered side walls 206 of the receiving portion 205 to compress against the locking collar 150, thereby causing the slot 166 to narrow. This radial inward compression causes the head 122 of the screw 120 to be crush locked to the inwardly curved interior surface 154 of the locking collar 150.

In addition, the rod is locked between the bottom surface 188 of the locking device 185 and the top surface 156 of the locking collar 150. This locking prevents the rod 250 from sliding relative to the assembled structure (along an axis which is perpendicular to the plane of FIG. 9). The full insertion of the top locking nut 185, therefore, locks the rod 250 in the channel of the receiving member 200, as well as the screw 120 within the locking collar 150.

Figure 10:
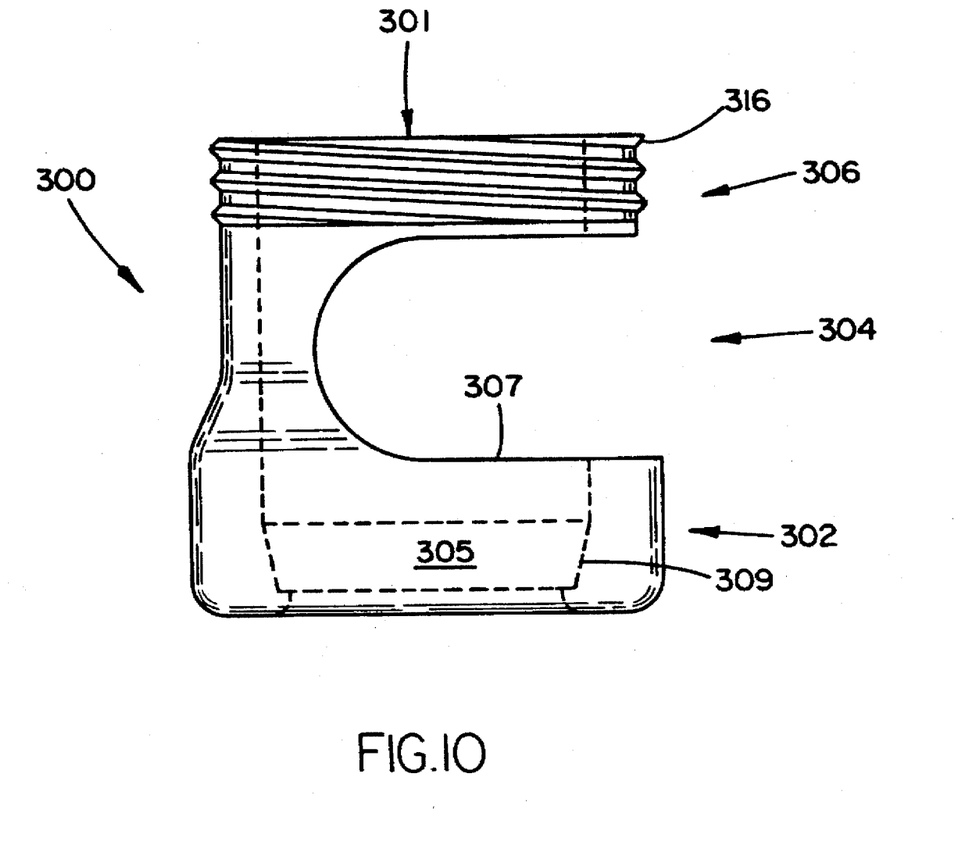
FIG. 10 is a side view of a second coupling element of the present invention having a side loading channel and wherein interior features of the element are shown in phantom.
Figure 11:
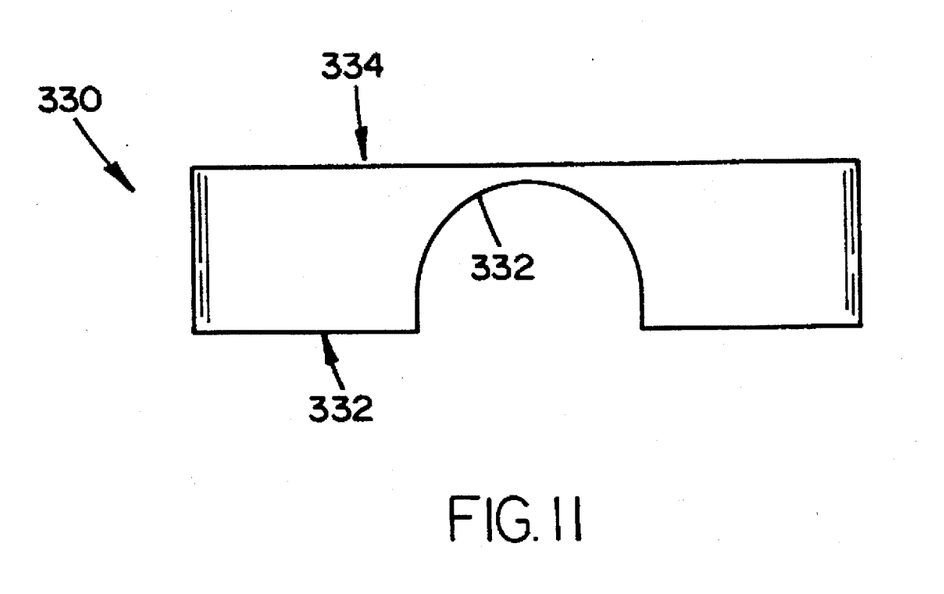
FIG. 11 is a side cross-sectional view of a rod securing sleeve which is utilized with the side loading embodiment of the present invention.
Figure 12:
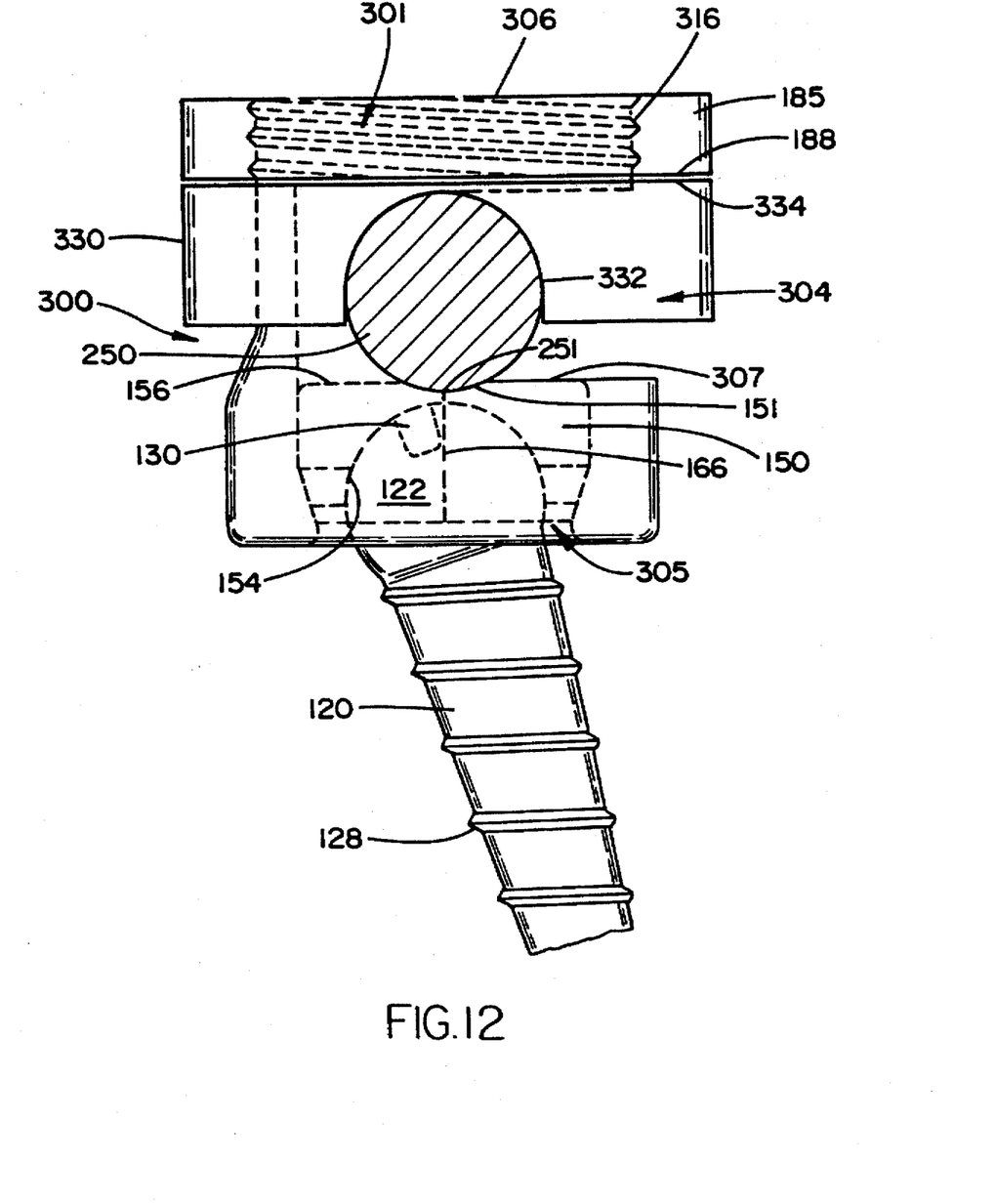
FIG. 12 is a side cross-sectional view of the side loading embodiment of the present invention in its fully assembled disposition having a rod securely locked therein.

Referring now to FIGS. 10, 11, and 12, an alternative, side loading variation of the invention is provided. Referring specifically to FIG. 10, a receiving member 300 having a channel formed in the side thereof is illustrated in a side view, wherein critical features thereof are shown in phantom. This receiving member comprises an axial bore 301 which is similar to the one in the first embodiment, through which the locking collar 150 may be inserted (the collar could be inserted through the channel in the alternative). The bottom of the axial bore 301 is tapered so that the locking collar may initially seat in the socket 305, and may be securely locked therein by the application of a downward force. The screw 120 is inserted upwardly through the bootom into the locking collar 150 once it is in place.

The receiving member comprises a lower portion 302, which is similar to the lower portion of the first coupling element 200, as set forth above with respect to FIGS. 6, 8 and 9. The remainder of the receiving member 300 is divided into an intermediate portion 304 and an upper portion 306. The intermediate portion includes the side channel into which the rod 250 is to be secured. In its initial disposition in the receiving portion 305 of the lower portion 302, the top surface 156 of the locking collar 150 extends upwards beyond the lower ledge 307 of the channel. The height of the channel is equal to, or greater than the width of the rod and the extent to which the top surface 156 of the collar 150 rises above the lower ledge 307. This permits the rod 250 to be inserted into the channel and subsequently for it to translate downward therein to force the locking collar 150 downward in the linearly tapered receiving portion 305 (thereby locking it securely therein).

The upper portion 306 of the receiving member 300 comprises a tubular section which includes the top of the axial bore 301, and an exterior threading 316 which is suitable for engagement of a locking device such as is set forth in FIGS. 7a and 7b.

Referring to FIG. 11, the rod securing sleeve 330 which is necessary for reliably holding the rod 250 in the channel is shown in a side view. The rod securing sleeve comprises a hollow cylindrical section, having an interior diameter which permits it to be dropped over the upper portion 306 of the receiving member 300, and a lower annular surface 332 which is shaped to cup the rod 250, and prevent its movement. The upper annular surface 334 of the sleeve 330 is suitably flat, so that the lower surface of the locking device may seat thereagainst and provide the downward force necessary to lock the entire system together.

Referring now to FIG. 12, in which the fully assembled second embodiment is shown in a side view, the assembly of this embodiment is described. As above, a pre-drilled hole is initially provided in the bone, into which it is desired that the screw 120 be disposed. The hole may be pre-tapped, or the external threading 128 of the screw 120 may include a self-tapping lead edge. The locking collar 150 is then translated downward, through the axial bore 301 of the receiving member 300, until it seats in the linearly tapered receiving portion 305 at the tapered bottom of the axial bore 301. The screw 120 is then inserted upwardly into the bottom of the receiving member 300 and into the interior volume 158 of the collar 150. At this point in the assembly process, the screw 120 and the locking collar 150 have the capacity to rotate relative to one another, while the seating of the locking collar 150 in the receiving portion 305 prevents relative motion of the collar and the receiving member. The top surface 156 of the locking collar 150 is disposed above the lower ledge 307 of the side channel of the intermediate portion 304 of the receiving member 300, such that the notches 151 of the collar 150 are generally aligned with the axis of the channel.

By orienting the locking collar 150 and the screw 120 coaxially, a screwdriving tool may engage the recess 130 in the head 122 of the screw 120 so that it may be driven into the preformed hole in the bone.

Subsequent to the screw 120 being driven into the hole, the receiving member 300 and the locking collar 150 may be rotated and angulated relative to the screw 120, to an angle such that support rod 250 may be properly nested within the side channel. In this initial disposition, however, the bottom 251 of the rod 250 seats on the top surface 156 of the locking collar 150 and not fully on the lower ledge 307 of the channel.

After the rod 250 has been appropriately positioned, a rod securing sleeve 330 is placed over the upper portion 306 of the receiving member 300 and dropped downward so that the bottom annular surface thereof may cup the top of the rod 250. Subsequently, the locking device 185 (or 190) is threaded onto the threading 316 until the lower surface 188 thereof seats against the upper annular surface 334 of the sleeve 330. As the locking device 185 rotates and descends relative to the receiving member 300, the rod securing sleeve 330 applies a downward force onto the rod 250, which is, in turn, driven downward, causing the rod 250 and the locking collar 150 to translate downward correspondingly. This downward translation causes the linearly tapered side walls of the receiving portion 305 to compress against the locking collar 150, thereby causing its slot 166 to narrow. This radial inward compression causes the head 122 of the screw 120 to be crush locked to the inwardly curved surface 154 of the locking collar 150.

In addition, the rod is securely locked between the bottom surface 334 of the rod securing sleeve 330 and the top surface 156 of the locking collar 150. This locking prevents the rod 250 from sliding relative to the assembled structure (along an axis which is perpendicular to the plane of FIG. 12). The full insertion of the locking device 185, therefore, locks the rod 250 in the channel of the receiving member 300, as well as the screw 120 within the locking collar 150.

While there has been described and illustrated embodiments of a polyaxial screw and receiving member assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A device for stabilizing spinal column segments, comprising:
    a pedicle screw having a threaded shaft portion and a semi-spherical head at the end of said threaded shaft portion;
    a locking collar having a semi-spherical interior volume for flexibly retaining said semi-spherical head, said locking collar having a linearly tapered cylindrical exterior surface;
    a receiver member having
        a rod receiving channel,
        a bore having first and second ends,
        a receiving chamber being provided at said second end, said chamber having a linear taper for receiving the locking collar, and
        an opening being provided opposite said bore, at said first end for inserting said locking collar through said bore, and
        said second end being provided to receive the head of said screw therethrough for positioning thereof in the semi-spherical interior volume of said locking collar, such that said shaft portion of said screw extends downwardly from said receiving member; and
    said device further comprising a compression member for exerting a force onto said locking collar such that said semi-spherical interior chamber contracts and is pressed against said semi-spherical head by cooperation between the tapered exterior surface and the chamber linear taper thereby compression locking said head to said locking collar.

2. The assembly as set forth in claim 1, wherein said channel comprises a recess in the side of the receiving member.

3. The assembly as set forth in claim 1, wherein the first end of said bore comprises a pair of upwardly extending members defining therebetween said channel.

4. The assembly as set forth in claim 1, wherein said locking collar further comprises at least one axial slot.

5. The assembly as set forth in claim 1, wherein said tapered exterior surface of said locking collar includes at least one circumferential arc section along a portion of its axial extent which is flat, and wherein said second end of said bore comprises a corresponding circumferential flat portion such that said locking collar may remain rotationally oriented in said axial bore.

6. The assembly as set forth in claim 1, wherein said top surface of said locking collar comprises a pair of notches for receiving thereon said rod.

7. The assembly as set forth in claim 1, wherein said receiving member further includes a threading formed on a surface thereof at the end of said receiving member which is proximal to the first end of said bore.

8. The assembly as set forth in claim 7, wherein said threading is formed on an inner surface of said bore at said first end.

9. The assembly as set forth in claim 7, wherein said threading is formed on an exterior surface of said receiving member.

10. The assembly as set forth in claim 7, wherein said compression member comprises a threaded means which engages said threads of said receiving member and locks said rod in said channel, thereby applying said force to said locking collar.

11. A orthopedic rod implantation apparatus having polyaxial screw and coupling elements, comprising:
    at least one elongate rod;
    a plurality of rod coupling assemblies, wherein at least one of said assemblies comprises,
        a pedicle screw having a threaded shaft portion and a semi-spherical head at the end of said threaded shaft portion;
        a locking collar having a semi-spherical interior volume for flexibly retaining said semi-spherical head, said locking collar having a linearly tapered cylindrical exterior surface;
        a receiver member having
            a rod receiving channel,
            a bore having first and second ends,
            a receiving chamber being provided at said second end, said chamber having a linear taper for receiving the locking collar, and
            an opening being provided opposite said bore, at said first end for inserting said locking collar through said bore, and
            said second end being provided to receive the head of said screw therethrough for positioning thereof in the semi-spherical interior volume of said locking collar, such that said shaft portion of said screw extends downwardly from said receiving member; and said device further comprising a compression member for exerting a force onto said locking collar such that said semi-spherical interior chamber contracts and is pressed against said semi-spherical head by cooperation between the tapered exterior surface and the chamber linear taper thereby compression locking said head to said locking collar.

12. The apparatus as set forth in claim 11, wherein said channel comprises a recess in the side of the receiving member.

13. The apparatus as set forth in claim 11, wherein the first end of said bore comprises a pair of upwardly extending members defining therebetween said channel.

14. The apparatus as set forth in claim 11, wherein said locking collar further comprises at least one axial slot.

15. The apparatus as set forth in claim 11, wherein said tapered exterior surface of said locking collar includes at least one circumferential arc section along a portion of its axial extent which is flat, and wherein said second end of said bore comprises a corresponding circumferential flat portion such that said locking collar may remain rotationally oriented in said bore.

16. The apparatus as set forth in claim 11, wherein said top surface of said locking collar comprises a pair of notches for receiving thereon said rod.

17. The apparatus as set forth in claim 11, wherein said receiving member further includes a threading formed on a surface thereof at the end of said receiving member which is proximal to the first end of said bore.

18. The apparatus as set forth in claim 17, wherein said threading is formed on an inner surface of said bore at said first end.

19. The apparatus as set forth in claim 17, wherein said threading is formed on an exterior surface of said receiving member.

20. The apparatus as set forth in claim 17, wherein said compression member comprises a threaded means which engages said threads of said receiving member and locks said rod in said channel, thereby applying said force to said locking collar.

* * * * *